United States Patent [19]

Seo et al.

[11] Patent Number: 5,847,257
[45] Date of Patent: Dec. 8, 1998

[54] TRANSGENIC MOUSE DEFICIENT IN T-CELLS

[75] Inventors: Jeong-Sun Seo; Soonhee Kim; Woong-Yang Park, all of Seoul, Rep. of Korea

[73] Assignee: Jeongsun SEO, Seoul, Rep. of Korea

[21] Appl. No.: 558,651

[22] Filed: Nov. 16, 1995

[30] Foreign Application Priority Data

Nov. 21, 1994 [KR] Rep. of Korea .................. 1994-30675

[51] Int. Cl.$^6$ ............................. C12N 5/00; C12N 15/00; C12N 15/09
[52] U.S. Cl. ......................... 800/2; 435/172.3; 435/69.1; 435/69.6; 435/694; 435/91.2; 435/320.1; 536/23.1; 536/23.5; 536/24.31; 935/23; 935/78; 935/79; 935/70; 935/71
[58] Field of Search .............................. 800/2; 435/172.3, 435/69.1, 69.6, 69.4, 91.2, 320.1; 536/23.1, 23.5, 24.31; 935/23, 78, 79, 70, 71

[56] References Cited

U.S. PATENT DOCUMENTS 5,087,571 2/1992 Leder et al. ........................ 435/240.2
5,175,383 12/1992 Leder et al. ................................ 800/2
5,175,384 12/1992 Krimpenfort et al. ...................... 800/2
5,175,385 12/1992 Wagner ...................................... 800/2

OTHER PUBLICATIONS

Morello et al., The EMBO Journal, vol. 5, pp. 1877–1883, 1986.

Hunt et al., Proclamation of the National Academy of Science, USA, vol. 82, pp. 6455–6459, 1985.

Uney et al., Society for Neuroscience Abstracts, vol. 18, p. 1145, 1992.

*Primary Examiner*—Jasemine C. Chambers
*Assistant Examiner*—Jill D. Schmuck
*Attorney, Agent, or Firm*—Nixon & Vanderhye, P.C.

[57] ABSTRACT

The present invention relates to a transgenic mouse deficient in T-cells, which is provided by fusing human heat shock protein (Hsp) gene with H2K promoter and transferring it to a mouse. Transgenic mouse line with a shrunken thymus and edficient in T-cells not having mature T-cells can be obtained.

5 Claims, 4 Drawing Sheets spleen leukocyte

TRANSGENIC MOUSE DEFICIENT IN T-CELLS

BACKGROUND OF THE INVENTION

1. Field of the Invention

The present invention relates to a transgenic mouse deficient in T-cell. More particularly, the invention relates to a transgenic mouse deficient in T-cell, which is produced by inserting a gene to express heat shock protein (Hsp) under the control of H2K promoter to in mouse.

2. Description of the Related Arts

A transgenic mouse is created by microinjecting a particular gene fragment to a fertilized egg of a mouse and introducing the fertilized egg to the womb of a mother mouse. By screening the tail DNA of the offspring 3 weeks after birth, it can be confirmed whether the gene is inserted to DNA in the cell of the offspring. A transgenic mouse is useful to identify functions of a gene. The transgenic mouse can be used as a model for many human diseases and as a bio-reactor which produces required genes, and also can be used for developing medicines against diseases.

Recently, the transgenic mouse technique as an approach to solve the various genetic problems, such as tumors has been developed. The success in producing c-myc oncogene-inserted transgenic mouse by P. Leder at Harvard University in the U.S.A. has drawn great attention in the field of human leukemia, and the first patent for a living organism was issued to this technique (U.S. Pat. No. 5,087,571). U.S. Pat. No. 5,175,383 issued to Philip Leder et al disclosed male mice with the giant prostate gland, and U.S. Pat. No. 5,175,384 issued to Paulus J. A. Krimpenfort et al discloses mice which cannot produce mature T-cells, and U.S. Pat. No. 5,175,385 issued to Thomas E. Wagner et al discloses mice which produce human, β-interferon.

The immune response is a complex defense system which recognizes and kills invading organisms such as bacteria or viruses, or unusual cells produced in self-tissues. The most characteristic aspects of the immune system are the specific recognition of antigens and the ability to discriminate between self- and non-self antigen. The system comprises a blood immune system by B-cell and a cellular immune system by T-cell. The lymphocyte of the peripheral blood includes 65–80% of T-cell and 8–15% of B-cell. T-cells exceed B-cells in number; moreover, the function relates to the total regulation of the immune system, for example, T-cells regulate antibody production and prevents injury to the target cell. The hematogeous liver cells of a bone marrow at embryonic stage pass through the thymus to become T-cells.

In the meantime, heat shock protein (Hsp) is an important protein in recovering damaged cells, is expressed in the state of heat shock or stress, and is produced at an embryogenic stage as well as a particular step of differentiation of cell and cell cycle. Also, H2K promoter is known as promoter activated in various cells, such as, spleen, pancreas, thymus, lung, etc. (Uirich et al, 1988, Cell, Vo. 53, pp. 847–856).

While conducting research on the influence of the Hsp expression on many organs and cell types, the present inventors have discovered that the thymus of a transgenic mouse was reduced in size and mature T-cells become deficient by transferring a rearranged Hsp gene and a H2K promoter to the mouse.

Accordingly, it is an object of this invention to provide transgenic mouse deficient in T-cells, which is produced by transferring the rearranged human Hsp gene and H2K promoter to the mouse.

SUMMARY OF INVENTION

The present invention provides a transgenic animal, such as a mouse, expressing the symptoms associated with a deficiency in the T-cell immune deficiency, characterized by a shrunken thymus, and having a recombinant DNA, wherein the DNA comprises a 2.0 kb HindIII-EcoRI fragment of human H2K promoter of human H2K gene, and a 2.3 kb Bam HI-HindIII fragment of human heat shock protein 70 gene operably linked to, and downstream of, said promoter. Further, the present invention provides a transgenic mouse comprising the recombinant DNA and expressing the recombinant DNA gene product in its germ cells and somatic cells, wherein said transgenic mouse exhibits symptoms associated with a deficiency in T-cells, such as a shrunken thymus.

Further, the present invention provides a process for preparing a transgenic mouse comprising the steps of inserting a recombinant DNA comprising a 2.0 kb HindIII-EcoRI fragment of human H2K promoter of human gene and a 2.3 kb BamHI-HindIII fragment of human heat shock protein 70 gene operably linked to, and downstream of, said fragment of promoter into a fertilized egg; transferring said fertilized egg to a foster mother mouse; and obtaining a founder mouse whose offspring expresses the recombinant DNA gene product in its germ cells and somatic cells, wherein said offspring exhibits symptoms associated with a deficiency in T-cells, such as shrunken thymus.

The recombinant DNA is inserted into the fertilized egg of the mouse at the embryonic stage.

The process further comprises the steps of mating the founder mouse with a normal mouse to obtain F1 trangenic mice, and mating said F1 transgenic mice expressing the recombinant DNA gene product in its germ cells and somatic cells, wherein said F1 transgenic mice exhibit symptoms associated with a deficiency in T-cells such as shrunken thymus among said F1 mice.

The thymus is greatly constructed and only residual materials or traces of structure which is similar to the thymus remain, and it is possible to obtain a transgenic mouse line in which mature T-cells are not discovered in the peripheral blood. The transgenic mouse line is useful for research for diseases which are related to the immune system, such as AIDS, as well as self-immune diseases, such as diabetes, immune inhibitors and novel drugs for the diseases.

The following is presented as an example, but does not limit the scope of the invention.

DETAILED DESCRIPTION OF THE DRAWINGS

Figure 1:
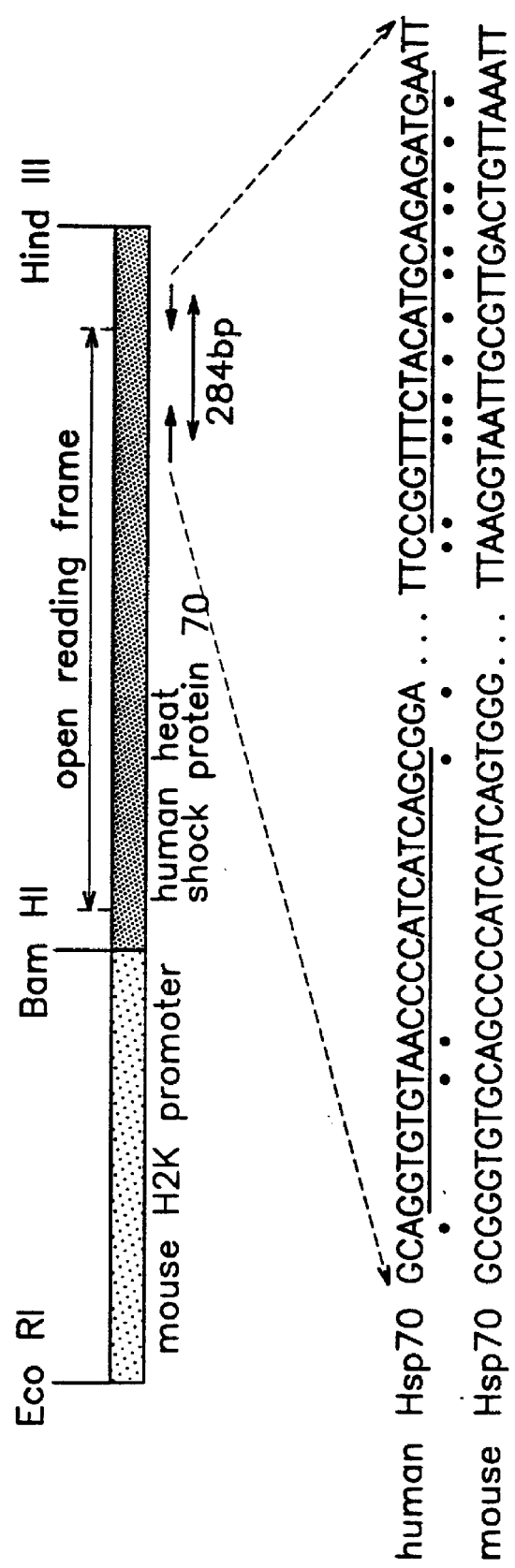
Figure 2:
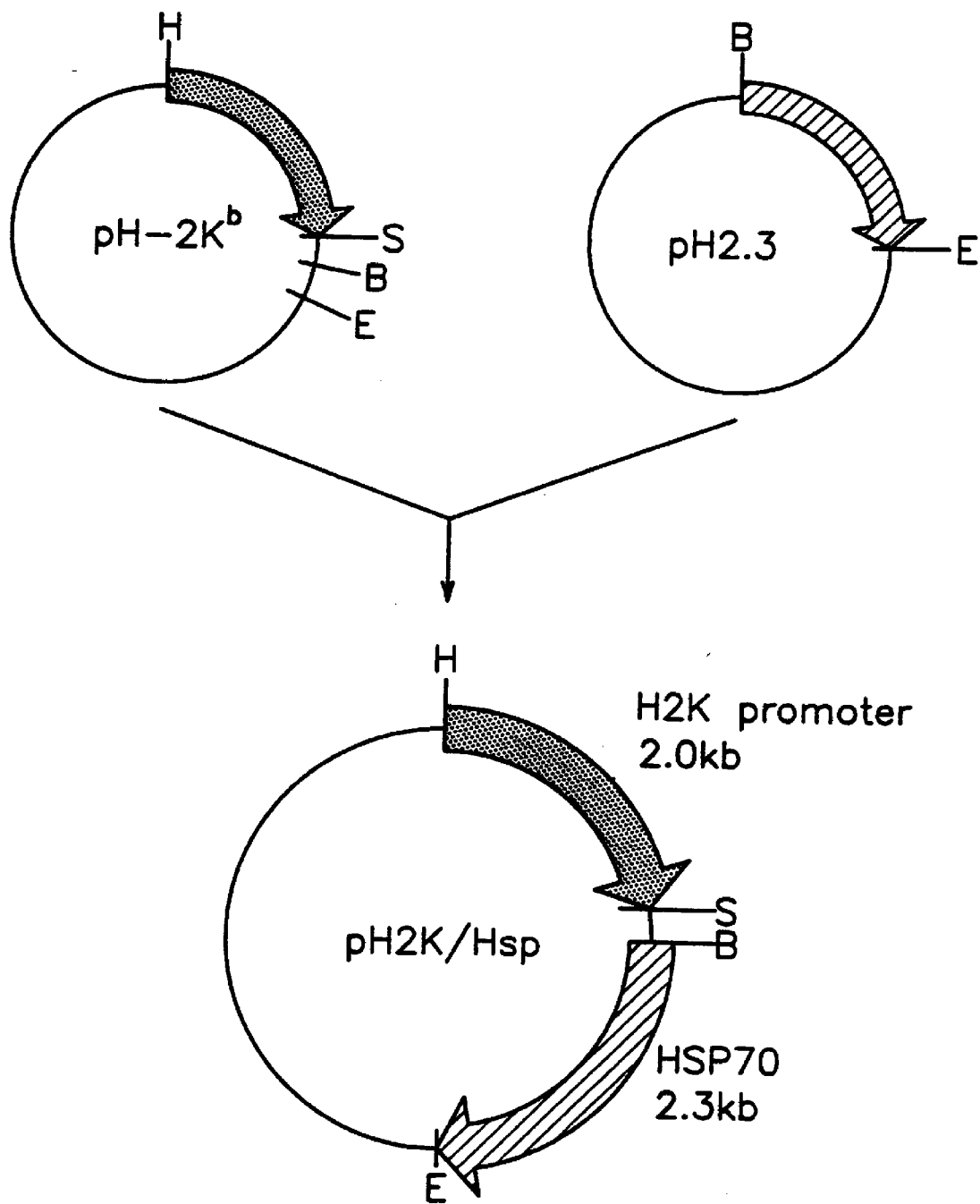
Figure 3:
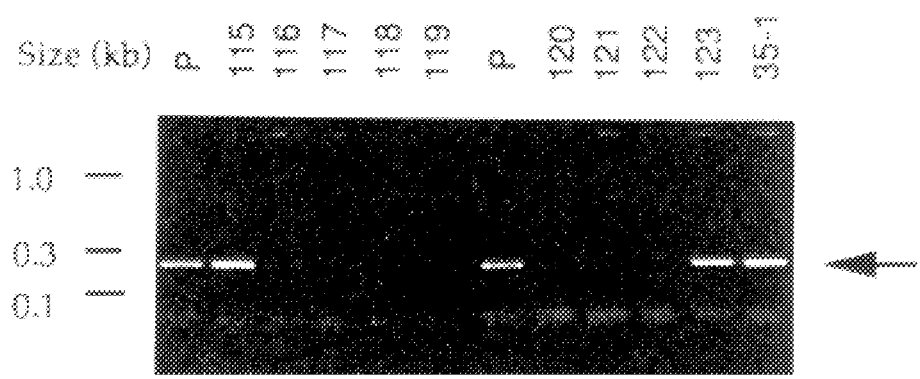

FIG. 1 shows broadly a gene constructed to express human Hsp 70 in the regulation of H2K promoter;

FIG. 2 demonstrates the rough construction process for human Hsp 70 gene expression vector;

FIG. 3 demonstrates the analysis of tail DNA of a transgenic mouse by PCR; and

Figure 4:
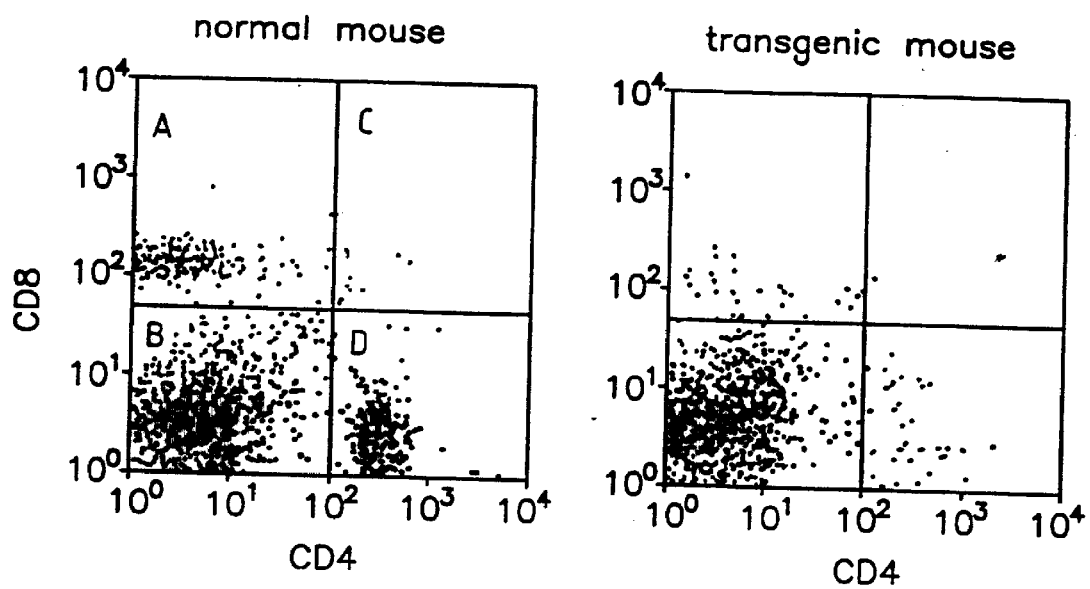
Figure 4:
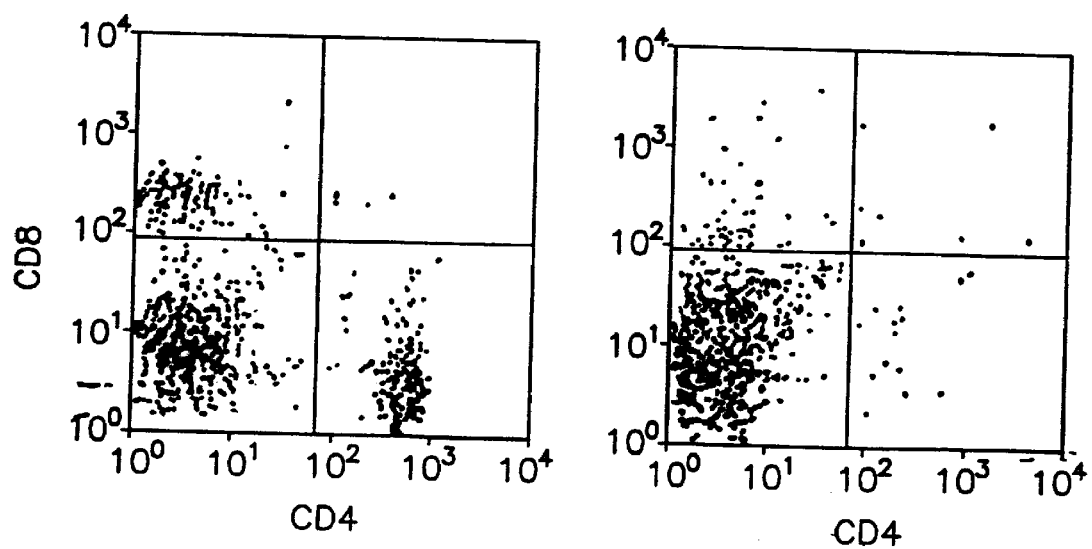

FIG. 4 illustrates the flow cytometry analysis of lymphocyte isolated from spleen and blood of a transgenic mouse.

EXAMPLE

Step 1. Construction of Human Hsp Gene Expression Vector pH2.3 (Hunt, C. & Morimoto, R. I., 1985, Proc, Natl. Acad. Sci. 82) was digested with BamHI and HindIII restriction enzyme to obtain human Hsp gene, and thereby a 2.3 kb DAN fragment was obtained. pH2K (Morello, D. et al, 1986, EMBO. J. 5, 1877–1883) was treated with HindIII and EcoRI to obtain 2.0 kb of H2K promoter. Two fragments were ligated to obtain 4.3 kb gene fragment (FIG. 1), then pH2K/HSP (FIG. 2) was prepared by cloning the 4.3 kb fragment on restriction enzyme (ECoRI and Hind III) site of pUC19 purchased from New England Biolabs. After transforming HB 101 E.coli by inserting pH2K/HSP to HB 101 E. Coli and the transformed E.coli was stored. The above E.coli was inoculated to ampicillin-containing LB medium (1% Bactotrypton, 0.5% Yeast Extract, 1% NaCl) to prepare a DNA solution for microinjection and cultured overnight at 37° C. The precipitate was centrifuged for 10 minutes at 2000 g, the resultant precipitate was collected, and dissolved in the solution of 50 mM glucose, 10 mM Tris-Cl, 1 mM EDTA, 4 mg/ml lysozyme and kept on the ice for 5 minutes. This solution was carefully mixed with 2 volumes of 0.2N NaOH and 1% SDS solution, kept for 5 minutes at room temperature, mixed with 0.5 volume of 5M potassium acetate solution, and kept on the ice for 5 minutes. The supernatant was obtained by centrifugation at 12000 g for 10 minutes. The supernatant was extracted with phenol and phenol / chloroform / isoamylalcohol (25:24:1) two or three times, and plasmid DNA was precipitated by adding 0.1 volume of 3M sodium acetate and 2 volumes of ethanol. The precipitated DNA was dissolved in TE buffer (10 mM Tris-CL, pH 8.0/1 mM EDTA, pH 8.0) and CsCl was added to have 1 g/ml of final concentration of CsCl. This solution was centrifuged at 100,000 rpm for 12 hours by Beckman TL 100 rotor for purification of DNA. The band including plasmid DNA was separated with an injector, extracted with n-butanol and dialysed for 24 hours against TE buffer. After plasmid DNA extraction, DNA was digested with restriction enzyme EcoRI, purified by excising agarose gel fragment containing H2K-Hsp 70 gene of 4.3 kb after electrophoresis on 0.8% agarose gel. The concentration of DNA was quantified and DNA was diluted with 10 mM Tris-Cl, pH 7.5/0.2 mM EDTA, pH 8.0 buffer to become 4 ng/$\mu$l of DNA, and the DNA was stored at $-20°$ C. to be used as an injector.

Step 2. Microinjection of H2K-Hsp Gene

A great number of fertilized eggs were obtained from a few of donor mice by superovulation of F1 hybrid line (C57BL X CBA) purchased by Korean Life Engineering Research Institute or a female mouse of inbred FVB strain purchased by B&K Co. (England). The F1 hybrid line and the female are over 6 weeks old. The best time to microinject the DNA to male pronucleus of fertilized egg cell is 1 cell cycle of fertilized egg of a mouse, the time depends on strain, supplier and light-dark cycle of animal room. F1 hybrid was used, and light-dark cycle of animal room was set to be turned off at 7:00 turned on at 6:00 a.m. and microinjection was started at 10:30 a.m. A fertilized egg was fixed at a position where a male pronucleus can be seen easily, and 1–2 pl DNA was injected to the male pronucleus with a pipet for injection.

Step 3. Insertion of a Microinjected Fertilized Egg to the Oviduct of Foster Mother Mouse Among the fertilized eggs in which the DNA was inserted, dissolved eggs were discarded and the healthy eggs were transferred to a foster mother mouse on the same day or cultured in inoculated to M16 medium at 37° C. in an incubator. The line of male mouse to be mated with a foster mother mouse was inbred ICR strain. The vasectomy was carried out for the male mouse, and the male mouse was used after ascertaining that an offspring was not brought forth in spite of having a vaginal plug when it was mated with another female mouse. An ICR female mouse close to ovulation period was mated with a male mouse after vasectomy, and if there were a vaginal plug, it was used as a foster mother mouse.

The operation was carried out by inoculating 0.2 ml of an anaesthetic, which is somnopentyl (64.8 mg sodium pentobarbital/ml produced by Pitman-Moore Co.) diluted 10 times with PBS, into the abdominal cavity. Then 20–25 fertilized eggs, to which DNA were microinjected were inserted to both oviducts, and the operated site was sutured.

Step 4. Breeding of transgenic mouse

A transgenic mouse was mated with a normal hybrid mouse (C57BL X CBA) or inbred FVB strain mouse which are more than 6 weeks old after confirming that H2K-Hsp 70 gene inserted into the transgenic mouse. Confirmation was accomplished by PCR of tail DNA of the mouse. Every morning, the vaginal plug was examined to check whether it has been fertilized and in case of abnormal mating, it was examined again after mating with another normal mouse. In 3–4 weeks, after birth (F1) of offspring, the transfer of H2K-Hsp70 gene of a foster mother mouse was screened by PCR of tail DNA. After screening the transfer of H2K-Hsp 70 gene, it was named as the transgenic mice line. Again, an F1 transgenic mouse was mated with a normal hybrid (C57BL X CBA) mouse or inbred FVB strain which was more than 6 weeks old.

In the meantime, the mating between the offspring of foster mother mice was carried out to prepare homozygote transgenic mice. An F3 mouse was obtained by mating an F2 transgenic mouse born in the above process with a normal hybrid (C57BL X CBA) mouse or inbred FVB strain mouse to search for homozygote of F2 transgenic mice, and examined the percentage of mice with H2K-Hsp 70 gene.

The morrhism analysis of a transgenic mouse deficient in T-cell

1) Tail DNA extraction

A polymer DNA was extracted from the tail of a mouse and transformation gene was screened by PCR. 1.5–2.0 cm tail end of a mouse which was about 3 4 weeks old was excised, finely cut off, added to 500 Ml buffer solution containing 50 mM of Tris-Cl, pH 8.0/50 mM of EDTA, and pH 8.0/0–5% of SDS. To this solution proteinase K was added to make concentration of 200 Mg/ml, and the mixture was reacted at 55° C. for 9 hours. The reactant was extracted with an equal volume of phenol and phenol/chloroform/isoamylalcohol (25:24:1) three times, and was dialysed against 10 mM of Tris-Cl, pH 8.0/1 mM of EDTA, pH 8.0 for 36 hours (12 hours x3 times). The DNA concentration was measured by a spectrophotometer and this DNA solution was stored at 4° C.

2) PCR analysis 77.5 ul of deionized water, 2 ul of sample DNA, each 2 ul of DATP, DGTP, DCTP, DTTP, 10 ul of Taq DNA polymerase buffer (100 mM Tris (pH 8.3)), 500 mM of KCl, 15 mM of MgCl12'0.1 t gelatine), 2 Ml of primer were mixed in a microfuge tube. The zone indicated as arrows in FIG. 1 represented the primer and the underlined zone represented the base sequence of the primer. Mineral oil was added to the supernatant of the above mixture solution,and the solution was heat-treated at 95° C. for 5 minutes to inactivate protease existing at DNA extraction solution. In the meantime, the temperature was adjusted to 70° C. to denature DNA enough. 0.5 Ml of Taq DNA polymerase (2.5 U) was added to the reaction mixture in each tube by passing through the oil layer, and PCR cycle of denaturation (94° C., 0.5–1 minute), annealing (55° C., 0.5–1 minute) and extending (72° C., 1 minute) was carried out 30 times. After a pertinent PCR cycle was completed, the final step was prolonged for 5 minutes so that the elongated DNA fragment could be induced and to form double helix. Then oil layer of the supernatant was removed, an equal volume of chloroform was added, the solution was centrifuged at 15,000 rpm for 5 minutes. The supernatant was transferred to a new tube, and 0.1 times of 3M NaOAc (pH 5.2) and 2.5 times of 95% EtOH were added thereto, and then the solution was frozen at −70° C. for 15 minutes and centrifuged at 15,000 rpm, at 40° C. for 15 minutes. The precipitation was added to 70% EtOH, washed, centrifuged for 5 minutes, the final PCR elongated DNA was dried in vacuum atmosphere, dissolved in 20 ul of TE buffer or distilled water and 1–2 ul thereof was tested by electrophoresis.

The experiment result is shown in FIG. 3. FIG. 3 shows that P was positive contrast group, and H2K-Hsp 70 gene were transferred to the above mice because the transgenic mice numbering 115, 123, 35 -1 showed the same bands with P.

3) Flow cytometry analysis of lymphocyte

To examine whether a transgenic mouse has been deficient in T-cell, lymphocyte was isolated from spleen and blood, where a lot of T-cells exist, and flow cytometry analysis was carried out using monoclonal antibody specific to T-cell markers CD-4 and CD-8 as shown in FIG. 4. The comparison between the results of normal mouse (left) and transgenic mouse (right), showed that the distribution phase was different from each other. Especially, because CD4 or CD8 always exists in T-cells in the presence of functional T-cells, CD4 or CD8 should be shown in A region (lymphocyte having CD8, not CD4) or D region (lymphocyte having CD4, not CD8 in normal mouse). As a transgenic mouse showed no marks in A region or D region, it can be assumed that there were no functional T-cells in a transgenic mouse.

---

What is claimed is:

1. A transgenic mouse lacking functional T-cells, wherein the germ cells and somatic cells of said mouse comprise recombinant DNA consisting of a 2.0 kb HindIII-EcoRI fragment of a human H2K gene promoter operably linked to a 2.3 kb BamHI-HindIII fragment of human heat shock protein 70 gene, and wherein expression of said human heat shock protein 70 in said mouse results in said mouse exhibiting a shrunken thymus and lacking functional T-cells.

2. A process for preparing the transgenic mouse of claim 1 comprising the steps of:

(I) introducing recombinant DNA consisting of a 2.0 kb HindIII-EcoRI fragment of a human H2K gene promoter operably linked to a 2.3 kb BamHI-HindIII fragment of human heat shock protein 70 gene into a fertilized egg or embryo of a mouse, (ii) inserting said egg or said embryo into the uterus of a foster mother mouse;

(iii) allowing said egg or said embryo to develop to term;

(iv) obtaining a founder mouse carrying said recombinant DNA; and (v) breeding said founder mouse with a normal mouse to obtain F1 offspring that express the human heat shock protein 70, and wherein said F1 offspring exhibit a shrunken thymus and lack functional T-cells.

3. The process of claim 1, wherein said recombinant DNA is introduced into a mouse embryo.

4. The process of claim 1, wherein said recombinant DNA is introduced into a fertilized mouse egg.

5. The process of claim 1, further comprising the step of mating two of said F1 offspring to obtain a homozygous transgenic mouse that expresses the human heat shock protein 70, and wherein said homozygous transgenic mouse exhibits a shrunken thymus and lacks functional T-cells.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCAGGTGTGT AACCCCATCA TCAGCGGA                                      28

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTCCGGTTTC TACATGCAGA GATGAATT                                      28

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCGGGTGTGC AGCCCCATCA TCAGTGGG                                      28

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:4:

TTAAGGTAAT TGCGTTGACT GTTAAATT 28